US007771746B2

(12) United States Patent
Mailland

(10) Patent No.: US 7,771,746 B2
(45) Date of Patent: Aug. 10, 2010

(54) METHODS FOR MAKING SUSTAINED-RELEASE PHARMACEUTICAL COMPOSITIONS OF ERGOT ALKALOIDS HAVING IMPROVED BIOAVAILABILITY AND COMPOSITIONS THEREOF

(75) Inventor: Federico Mailland, Milan (IT)

(73) Assignee: Polichem SA, Val Fleuri (LU)

( * ) Notice: Subject to any disclaimer, the term of this patent is extended or adjusted under 35 U.S.C. 154(b) by 1326 days.

(21) Appl. No.: 10/992,114

(22) Filed: Nov. 19, 2004

(65) Prior Publication Data

US 2005/0202087 A1    Sep. 15, 2005

Related U.S. Application Data

(63) Continuation-in-part of application No. 10/016,005, filed on Nov. 2, 2001, now abandoned, which is a continuation of application No. 09/454,364, filed on Dec. 3, 1999, now abandoned.

(51) Int. Cl.
*A61K 9/20* (2006.01)
*A61K 9/22* (2006.01)

(52) U.S. Cl. ............ 424/468; 424/425; 424/470; 424/480

(58) Field of Classification Search ............ 424/464, 424/469, 468, 470
See application file for complete search history.

(56) References Cited

U.S. PATENT DOCUMENTS

| 3,752,888 | A | * | 8/1973  | Fluckiger et al. ............ 514/250 |
|-----------|---|---|---------|--------------------------------------|
| 3,896,228 | A |   | 7/1975  | Richardson ................. 424/266 |
| 3,987,173 | A |   | 10/1976 | Borredon .................... 424/261 |
| 4,229,451 | A |   | 10/1980 | Fehr et al. ................... 424/250 |
| 4,315,937 | A | * | 2/1982  | Maclay et al. ............... 514/250 |
| 4,366,145 | A |   | 12/1982 | Stoopak et al. .............. 424/37  |
| 4,369,172 | A |   | 1/1983  | Schor et al. ................ 424/19  |
| 4,389,393 | A |   | 6/1983  | Schor et al. ................ 424/19  |
| 4,440,772 | A |   | 4/1984  | Djordjevic et al. ......... 424/261  |
| 4,462,983 | A | * | 7/1984  | Azria et al. ................ 424/45  |
| 4,540,566 | A |   | 9/1985  | Davis et al. ................ 424/22  |
| 4,695,591 | A |   | 9/1987  | Hanna et al. ............... 514/781 |
| 4,737,499 | A |   | 4/1988  | Giger ....................... 514/250 |
| 4,828,836 | A |   | 5/1989  | Elger et al. ................ 424/419 |
| 4,935,429 | A |   | 6/1990  | Dackis et al. .............. 514/288  |
| 5,069,911 | A | * | 12/1991 | Zuger ....................... 424/469 |
| 5,128,142 | A |   | 7/1992  | Mulligan et al. ............ 424/457 |
| 5,192,550 | A | * | 3/1993  | Edgren et al. .............. 424/473 |
| 5,430,021 | A |   | 7/1995  | Rudnic et al. .............. 514/14  |
| 5,447,729 | A |   | 9/1995  | Belenduik et al. .......... 424/490 |
| 5,451,409 | A |   | 9/1995  | Rencher et al. ............ 424/468 |
| 5,582,837 | A |   | 12/1996 | Shell ....................... 424/451 |
| 5,622,722 | A |   | 4/1997  | Knott et al. ................ 424/494 |
| 5,631,021 | A |   | 5/1997  | Okada et al. .............. 424/451 |
| 5,716,928 | A |   | 2/1998  | Benet et al. ................ 514/11  |
| 5,840,332 | A |   | 11/1998 | Lerner et al. .............. 424/464 |
| 6,943,080 | B2|   | 9/2005  | Maruyama                             |

FOREIGN PATENT DOCUMENTS

| EP | 0 280 613 | 8/1988  |
| EP | 0 284 849 | 10/1988 |
| EP | 0 875 245 | 11/1998 |
| FR | 2 327 764 | 5/1977  |
| FR | 76 30866  | 5/1977  |
| GB | 2 170 407 | 8/1986  |

OTHER PUBLICATIONS

Halliburton Energy Services, Inc., International Application No. PCT/US04/38794, Patent Cooperation Treaty International Search Report mailed Jan. 24, 2006, 2 pages.
International Search Report; PCT/EP00/12302.
Abstract, XP-002168552, Database WPI, Section Ch, Week 198608, Derwent Publications, Ltd.

* cited by examiner

*Primary Examiner*—Michael G Hartley
*Assistant Examiner*—Micah-Paul Young
(74) *Attorney, Agent, or Firm*—Nixon & Vanderhye

(57) ABSTRACT

A method of improving bioavailability of ergot derivatives administered using sustained-release delivery systems includes combining an ergot derivative or mixture thereof with a pharmaceutically acceptable hydrophilic swelling agent or mixture thereof and one or more pharmaceutically acceptable excipients. The bioavailability of sustained-release formulations of the present invention is at least equal to the bioavailability of the ergot derivative or mixture thereof administered using a conventional delivery system. Sustained-release compositions that improve bioavailability are also provided. Methods and compositions according to the present invention may provide sustained-release characteristics while improving the bioavailability of ergot derivatives.

9 Claims, 1 Drawing Sheet

METHODS FOR MAKING SUSTAINED-RELEASE PHARMACEUTICAL COMPOSITIONS OF ERGOT ALKALOIDS HAVING IMPROVED BIOAVAILABILITY AND COMPOSITIONS THEREOF

This application is a Continuation-In-Part of application Ser. No. 10/016,005, filed Nov. 2, 2001, now abandoned which is a Continuation of application Ser. No. 09/454,364, filed Dec. 3, 1999, now abandoned the entire contents of which are hereby incorporated by reference in this application.

FIELD OF THE INVENTION

This invention relates to methods for making sustained-release pharmaceutical compositions of ergot alkaloids, and particularly to methods for making sustained-release pharmaceutical compositions of ergot alkaloids having improved bioavailability.

BACKGROUND OF THE INVENTION

In general, ergot alkaloids can be classified according to their different chemical structures, for example ergolines, lysergic acid derivatives, ergot peptide alkaloids and dihydrogenated ergot peptide alkaloids. Clinical applications of ergot alkaloids and their derivatives include treatment of Parkinson's disease, migraine headaches, hyperprolactinemia and cerebro-vascular disturbances, just to name a few.

Many ergot alkaloids and their derivatives are known. For example, U.S. Pat. No. 3,896,228 to Richardson discusses the use of ergot alkaloids to increase urine volume and urine pH. U.S. Pat. No. 3,987,173 to Borredon proposes the use of certain mixtures of vincamine and ergot alkaloids to treat blood circulation disorders. U.S. Pat. No. 4,229,451 to Fehr et al. provides ergopeptine derivatives useful as venoconstrictors and venotonics. U.S. Pat. No. 4,315,937 to Maclay et al. discusses ergots and their use in treating minimal brain dysfunction. U.S. Pat. No. 4,366,145 to Stoopak et al. discusses a soft gelatin capsule with a liquid ergot alkaloid center fill solution. U.S. Pat. No. 4,440,722 to Djorjevic et al. provides a medicine containing salts of ergotamine, ergosinine, ergocryptinine, ergocristinine and ergocominine used for treating arterial hypertension, heart insufficiency, heart arrhythmia or cephalalgia. U.S. Pat. No. 4,462,983 to Azria et al. proposes the use of certain ergot peptide alkaloids adapted for nasal or pulmonary administration.

The pharmacological actions of ergot alkaloids are varied and complex, but in general appear to result from their actions at adrenergic, dopaminergic and serotoninergic receptors. The spectrum of effects depends on the agent, dosage, species, tissue, and experimental or physiological conditions. In general, ergot alkaloids are characterized by erratic absorption and a high hepatic first pass effect with wide biotransformation. More specifically, gastrointestinal absorption of ergot alkaloids is low, due to the high hepatic first pass, and sometimes erratic. Moreover, the administration of ergot alkaloids can occasionally be associated with adverse events, particularly vascular and cardiac. Drugs, such as ergot alkaloids, that are susceptible to high hepatic clearance may need to be administered in higher doses in order to maintain blood concentrations above the minimum effective concentration for a sufficient amount of time to provide the desired pharmacological effect. However, when conventional drug delivery systems are used, the burst of drug absorption that occurs just after its administration may cause blood concentrations to exceed the minimum toxic concentration. One method of avoiding this deleterious effect is to employ lower dosage levels with more frequent dosing. Frequent dosing is not an ideal solution, however, because of the inconvenience, the increased cost and the increased likelihood that the patient will forget to take the proper number of doses. Another method of keeping drug concentration on a narrow therapeutically active level is to administer the drug using sustained-release drug delivery systems.

Sustained-release drug delivery systems include any drug delivery system that achieves slow release of the drug over an extended period of time. There are two general types of sustained-release systems: controlled-release and prolonged-release. Controlled-release systems maintain constant drug levels in the target tissue or cells. Prolonged-release systems are unable to maintain a constant drug level, but nevertheless prolong the therapeutic blood or tissue level of the drug for an extended period of time.

When designing sustained-release delivery systems many variables may be considered including the route of drug delivery, the type of delivery system, the specific properties of the drug being administered, and the bioavailability of the drug. Sustained-release delivery systems have been proposed for a number of different drugs. For example, U.S. Pat. No. 4,389,393 to Schor et al. proposes sustained release therapeutic compositions based on high molecular weight hydroxypropylmethylcellulose. U.S. Pat. No. 5,069,911 to Züger proposes a controlled release formulation for oral administration of a 9,10-dihydro ergot alkaloid, U.S. Pat. No. 5,128,142 to Mulligan et al. proposes a controlled release formulation that includes an absorbate of a mixture of a pharmaceutically useful active ingredient and an inactive substance adsorbed on a cross-link polymer.

While these references propose sustained-release delivery systems that may provide slow release of a particular drug over an extended period of time, they fail to provide such a system that also maintains or increases the bioavailability of the administered drug as compared to conventional delivery systems.

SUMMARY OF THE INVENTION

It is therefore an object of the present invention to provide sustained-release drug delivery systems that maintain or increase the bioavailability of the administered drug as compared to conventional delivery systems.

It is another object of the present invention to provide methods of forming such delivery systems.

These and other objects are provided, according to the present invention, by a method of improving bioavailability of ergot derivatives that includes combining an ergot derivative or mixture thereof with a pharmaceutically acceptable hydrophilic swelling agent or mixture thereof and one or more pharmaceutically acceptable excipients.

According to the present invention, the bioavailability is at least equal to the bioavailability of the ergot derivative or mixture thereof administered using a conventional delivery system.

In a preferred embodiment, the ergot derivative has the formula

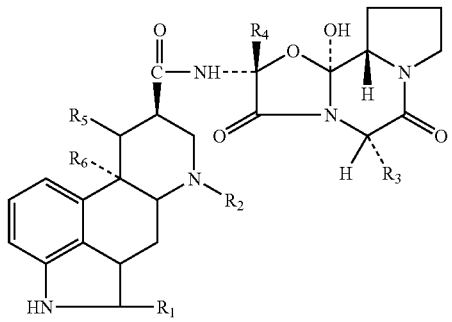
(I)

wherein:
- $R_1$ is hydrogen or halogen,
- $R_2$ is hydrogen or $C_1$-$C_4$ alkyl,
- $R_3$ is isopropyl, sec.-butyl, isobutyl or benzyl,
- $R_4$ is methyl, ethyl, isopropyl, and mixtures thereof, and either
- $R_5$ is hydrogen and
- $R_6$ is hydrogen or methoxy, or
- $R_5$ and $R_6$ together is an additional bond, and mixtures thereof.

According to the present invention, a pharmaceutical composition may also be provided. The composition has a bioavailability at least equal to the bioavailability of the ergot derivative or mixture thereof administered using a conventional delivery system.

Methods and pharmaceutical compositions according to the present invention may therefore provide sustained-release characteristics while improving the bioavailability of ergot derivatives.

DETAILED DESCRIPTION OF PREFERRED EMBODIMENTS

Figure 1:
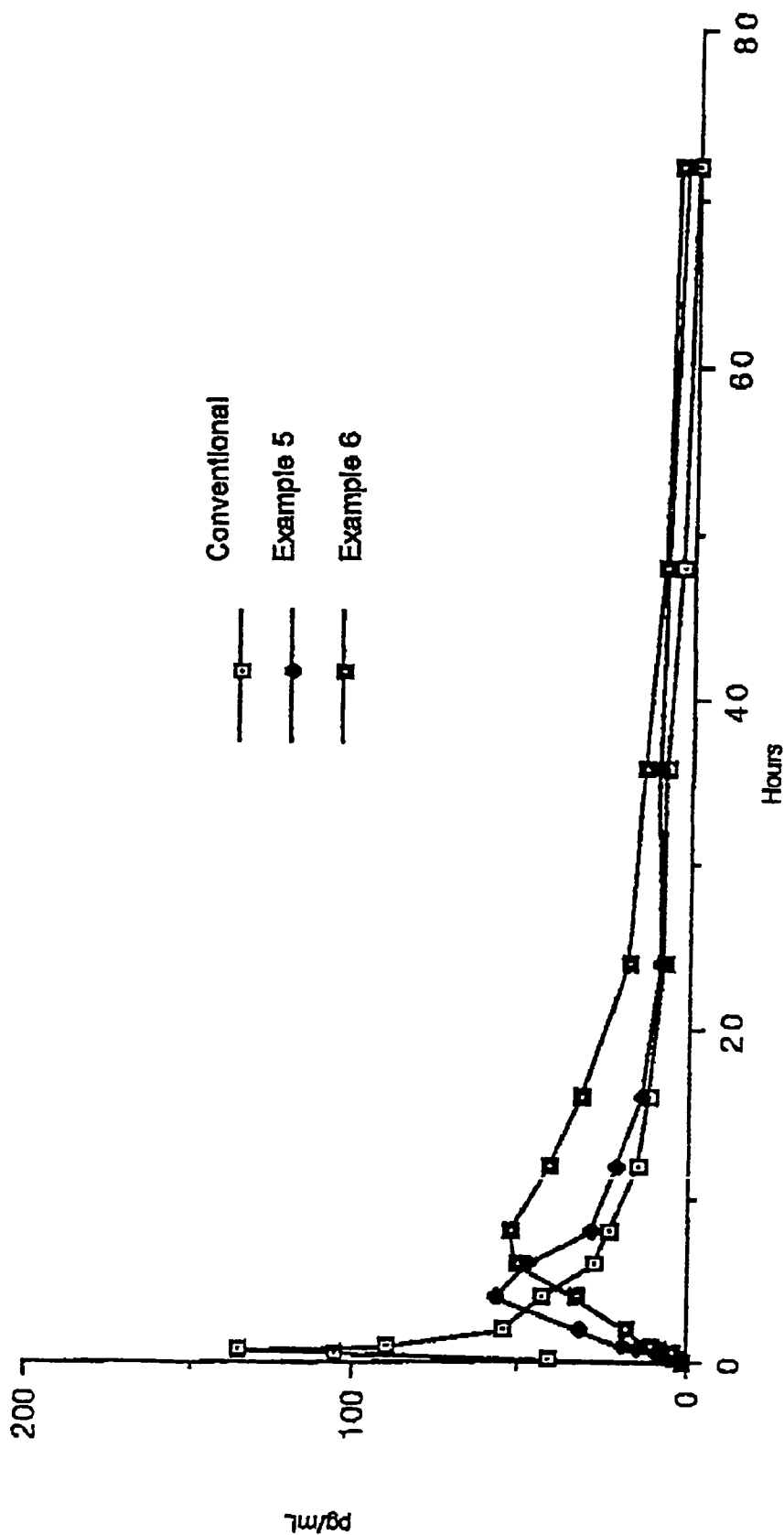
FIG. 1 is a graph of plasma concentration of α-dihydroergocryptine versus time after a single oral administration of 10 mg of α-dihydroergocryptine administered in a conventional tablet or in sustained-release tablets formulated according to the present invention as described in examples 5 or 6.

The present invention now will be described more fully hereinafter, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention provides a sustained-release composition of ergot derivatives having an improved bioavailability over conventional compositions. The sustained-release composition of the present invention comprises an ergot derivative or mixture thereof, a pharmaceutically acceptable swelling agent or mixture thereof, and one or more pharmaceutically acceptable excipients.

As used herein, bioavailability is defined as the total amount of drug systemically available over time. Bioavailability may be determined by measuring total systemic drug concentrations over time after administration of a sustained-release composition of the present invention and after administration of a conventional release composition. The improved bioavailability is defined as an increase in the Area Under the Curve (AUC). AUC is the integrated measure of systemic drug concentrations over time in units of mass-time/volume. Following the administration of a drug dose, the AUC from the time of dosing to the time when no drug remains in the body, is a measure of the exposure of the patient to the drug.

Ergot derivatives of the present invention may be various ergot derivatives known to those skilled in the art. Preferably, ergot derivatives are ergot alkaloids. The preferred ergot alkaloids are ergot peptide alkaloids and dihydrogenated ergot peptide alkaloids. A particularly preferred ergot alkaloid has the formula:

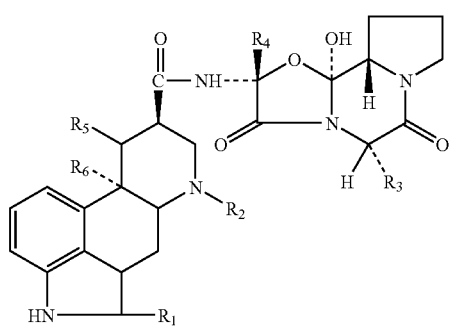
(I)

wherein
- $R_1$ is hydrogen or halogen,
- $R_2$ is hydrogen or $C_1$-$C_4$ alkyl,
- $R_3$ is isopropyl, sec.-butyl, isobutyl or benzyl,
- $R_4$ is methyl, ethyl, isopropyl, and mixtures thereof, and either
- $R_5$ is hydrogen and
- $R_6$ is hydrogen or methoxy, or
- $R_5$ and $R_6$ together is an additional bond, and mixtures thereof.

or mixtures thereof.

When $R_1$ is halogen, it is preferably bromine.

Preferred compounds of Formula I are those in which $R_1$, $R_5$ and $R_6$ are hydrogen, $R_2$ is methyl, and $R_4$ is isopropyl or methyl, provided that $R_4$ is methyl only when $R_3$ is benzyl.

Particularly preferred compounds in which $R_2$ is methyl and $R_1$, $R_5$ and $R_6$ are hydrogen are α-dihydroergocryptine ($R_4$=isopropyl, $R_3$=isobutyl), β-dihydroergocryptine ($R_4$=isopropyl, $R_5$=sec.-butyl), dihydroergocornine ($R_3$=$R_4$=isopropyl), dihydroergocristine ($R_4$=isopropyl, $R_3$=benzyl) and dihydroergotamine ($R_4$=methyl, $R_3$=benzyl), together with their salt forms. The preferred compound in which $R_1$ is bromine is bromocriptine, $R_2$=methyl, $R_3$=isobutyl, $R_4$=isopropyl and $R_5$ and $R_6$ are a second bond. Suitable salt forms are salts of pharmacologically acceptable acids; for example, the methanesulfonate, maleate and tartrate salt forms. The most preferred compound is dihydroergocriptine, usually employed in the form of mesylate. It is indicated for use in the treatment of Parkinson's disease, hyperprolactinemia and migraine. The drug may be administered twice a day at a daily dosage of about 10 to about 60 mg, preferably about 20 to about 40 mg.

Pharmaceutically acceptable swelling agents of the present invention are typically hydrophilic polymers, such as gums, cellulose ethers and protein derived materials. Preferably, these hydrophilic polymers may include hydroxyalkylcelluloses, polyvinyl alcohols, polyoxyethylene glycols, carbomers and poloxamers. Preferred hydroxyalkylcelluloses include methylcellulose, carboxymethylcellulose, hydroxypropylcellulose and hydroxypropylmethylcellulose.

The most preferred hydrophilic swelling substance is hydroxypropylmethylcellulose. Hydroxypropylmethylcelluloses that may be used in the present invention include Methocel K4M® and Methocel K15M®, both commercially available from Colorcon of West Point, Pa. Methocel K4M® and Methocel K15M® have a 19-24 weight percent methoxyl content and a 4-12 weight percent hydroxypropyl content. Methocel K4M® in a 2% water solution has a viscosity of 4,000 cps and an average molecular weight of 89,000, while Methocel K15M® in the same conditions has a viscosity of 15,000 cps and an average molecular weight of 124,000.

Formulations of the present invention also contain excipients. In general, excipients include lubricants, suspending agents, binders, diluents, flavorants, colorants, dispersing agents and wetting agents, the use of which will be known to those skilled in the art. Suitable excipients are, in particular, fillers such as sugars, including lactose, sucrose, mannitol, or sorbitol; cellulose preparations such as, for example, microcrystalline cellulose, maize starch, wheat starch, rice starch, potato starch, gelatin, tragacanth gum and/or polyvinylpyrrolidone (PVP); and lubricants such as magnesium stearate.

Formulations of the present invention preferably contain about 5 to about 80 mg of ergot peptide alkaloids. The ratio of ergot peptide alkaloid to swelling substance is preferably from about 1:0.5 to about 1:10, more preferably from about 1:2 to about 1:8. The ratio of dihydroergocriptine to swelling substance is from about 1:0.5 to about 1:5, more preferably from about 1:1 to about 1:4. The ratio of ergot peptide alkaloid to excipients is preferably from about 1:3 to about 1:100, more preferably from about 1:5 to about 1:80 and most preferably from about 1:10 to about 1:50.

Formulations of the present invention provide an increase in bioavailability over other sustained-release formulations. More importantly, formulations of the present invention provide an increase in bioavailability over conventional formulations. The bioavailability of formulations of the present invention is preferably at least about 5%, more preferably at least about 15%, and most preferably at least about 25% higher than the bioavailability of conventional formulations.

The formulations of the present invention may be prepared according to conventional methods by blending together the drug and all the excipients except the lubricant to form a blended powder. The powder is mixed with the lubricant and the resultant powder is pressed to form a tablet.

The following examples are provided to illustrate the present invention, and should not be construed as limiting thereof. In these examples, "mg" means milligram, "ng" means nanogram, "pg" means picogram, "mL" means milliliter, "mm" means millimeter, "° C." means degrees Celsius, "M" means mean, "SD" means standard deviation, "mPa·s" means milliPascal·seconds, "PVP" means polyvinylpyrrolidone, "h" means hour and "kp" means kiloponds.

Examples 1-6 Comparing Release Characteristics of FORMULATIONS OF THE PRESENT INVENTION WITH Release Characteristics of Conventional Formulations Example 1

α-Dihydroergocryptine 20 mg Sustained-Release Tablets

Composition of Each Tablet

| | |
|---|---|
| α-Dihydroergocryptine | 20.0 mg |
| Cellactose ® | 203.0 mg[1] |
| Methocel K15M ® | 25.0 mg[2] |
| Syloid 244 ® | 1.2 mg[3] |
| Magnesium stearate | 0.8 mg |

Notes:
[1]75% lactose and 25% microcrystalline cellulose, commercially available from Meggle GmbH of Wasserburg, Germany.
[2]Hydroxypropylmethylcellulose USP type 2208; 15,000 mPa · s, commercially available from Colorcon of West Point, Pennsylvania.
[3]Silicon dioxide, commercially available from W.R. Grace of Baltimore, Maryland.

Experimental Method

Tablets (250 mg) containing 20 mg (8%) each of α-dihydroergocryptine were prepared with 80% of Cellactose®, as direct compressible excipient, 10% of Methocel K15M®, as swellable controlled release polymer, 1.2% of Syloid 244®, as free flowing agent, and 0.8% of magnesium stearate, as lubricant. The drug and all excipients except the lubricant were geometrically blended manually with a sieve, then mixed with a Turbula mixer for 10 minutes. After adding magnesium stearate, the mixture was blended for another 5 minutes. A rotary 8-station laboratory press with automatic powder feed and capsular tools (12×5 mm) was used for compression.

Tablet Testing

Standard pharmaceutical test methods and equipment were used to determine the following:

Hardness: average of 18.6 kp (Schleuniger 4M)

Friability: 0.081%

Dissolution test, according to USP XXIII, p. 1792, Apparatus 2, 1000 ml H$_2$O, 50 rotations/min:

| Time (hours) | % Release of α-Dihydroergocryptine (M ± SD) |
|---|---|
| 0.5 | 12.7 ± 0.5 |
| 1 | 23.8 ± 1.4 |
| 2 | 32.6 ± 3.0 |
| 4 | 55.1 ± 6.0 |
| 6 | 72.2 ± 4.5 |
| 8 | 84.7 ± 6.3 |

The conventional tablet formulation of α-dihydroergocryptine 20 mg had the following composition: α-dihydroergocryptine, 20.0 mg; lactose, 148 mg; microcrystalline cellulose, 70 mg; croscarmellose, 6 mg; magnesium stearate, 4 mg; and polyvinylpyrrolidone, 2 mg. The dissolution test was carried out in the same conditions as for the sustained-release formulation of the present invention described in this example and resulted in 96.3±3.6% release of α-dihydroergocryptine after 0.5 hours.

Example 2

α-Dihydroergocryptine 20 mg Sustained-Release Tablets

Composition of Each Tablet

| | |
|---|---|
| α-Dihydroergocryptine | 20.0 mg |
| Methocel K4M ® | 13.2 mg[1] |
| Sodium CMC | 26.8 mg |
| Lactose | 48.0 mg |
| PVP K30 | 6.7 mg |
| Talc | 4.0 mg |
| Magnesium stearate | 1.3 mg |

Notes:
[1]Hydroxypropylmethylcellulose USP type 2208; 4,000 mPa · s, commercially available from Colorcon of West Point, Pennsylvania.

Experimental Method

Tablets (120 mg) containing 20 mg (16.7%) each of α-dihydroergocryptine were prepared and tested according to the methods described hereafter. The formulation was prepared with 40% of lactose, as diluent, 11% of Methocel K4M® and 22.3% of Sodium CMC (medium viscosity), as swellable controlled release polymers, 5.6% of PVP, as binding agent, 3.3% of talc, as anti-sticking agent, and 1.1% of magnesium stearate, as lubricant.

A 10% water solution of PVP was prepared. The drug, the diluent and the polymers were mixed coarsely. The water solution of PVP was added to the powder mix to form a wet mass, which was screened successively through 8 mesh screen. The wet granulate was dried at 60° C., then screened again through 16 mesh screen. After adding talc and magnesium stearate, the mixture was blended for five minutes in a V mixer. A rotary 8 station laboratory press with automatic powder feed and flat tools, diameter 7 mm, was used for compression.

Tablet Testing

Standard pharmaceutical test methods and equipment were used for determining the following:

Hardness: average of 11.2 kp (Schleuniger 4M)

Friability: 0.12%

Dissolution test, according to USP XXIII, p. 1792, Apparatus 2, 1000 ml $H_2O$, 50 rotations/min:

| Time (hours) | % Release of α-Dihydroergocryptine (M ± SD) |
|---|---|
| 0.5 | 12.9 ± 3.6 |
| 1 | 20.8 ± 6.3 |
| 2 | 22.7 ± 6.9 |
| 4 | 35.9 ± 7.7 |
| 6 | 47.6 ± 7.9 |
| 8 | 58.2 ± 10.1 |
| 12 | 68.4 ± 8.0 |

The conventional tablet formulation of α-dihydroergocryptine 20 mg had the same composition as in Example 1. The dissolution test was carried out in the same conditions as for the sustained-release formulation of the present invention described in this example and resulted in 98.1±5.2% release of α-dihydroergocryptine after 0.5 hours.

Example 3

α-Dihydroergocryptine 40 mg Sustained-Release Tablets

Composition of Each Tablet

| | |
|---|---|
| α-Dihydroergocryptine | 40.0 mg |
| Lactose DCL11 ® | 92.5 mg[1] |
| Avicel PH101 ® | 76.0 mg[2] |
| Methocel K4M ® | 37.5 mg[3] |
| Magnesium stearate | 4.0 mg |

Notes:
[1]Spray Dried Lactose produced by Meggle GmbH of Wasserburg, Germany.
[2]Microcrystalline cellulose, commercially available from FMC Corporation, Pharmaceuticals Division, of Philadelphia, Pennsylvania.
[3]Hydroxypropylmethylcellulose USP type 2208, 4,000 mPa · s, commercially available from Colorcon of West Point, Pennsylvania.

Experimental Method

Tablets (250 mg) containing 40 mg (16%) each of α-dihydroergocryptine were prepared and tested according to the methods described hereafter. The formulation was prepared with 37% of lactose and 30.4% of microcrystalline cellulose, as direct compressible excipients, 15% of Methocel K4M®, as swellable controlled release polymer, and 1.6% of magnesium stearate, as lubricant.

The drug and all excipients except the lubricant were geometrically blended manually with a sieve, then mixed with a Turbula mixer for 10 minutes. After adding magnesium stearate, the mixture was blended for another 5 minutes. A rotary 8 station laboratory press with automatic powder feed and capsular tools (12×5 mm) was used for compression.

Tablet Testing

Standard pharmaceutical test methods and equipment were used to determine the following:

Hardness: average of 14.9 kp (Schleuniger 4M)

Friability: 0.072%

Dissolution test, according to USP XXIII, p. 1792, Apparatus 2, 1000 ml $H_2O$, 50 rotations/min:

| Time (hours) | % Release of α-Dihydroergocryptine (M ± SD) |
|---|---|
| 0.5 | 12.5 ± 0.6 |
| 1 | 22.1 ± 1.4 |
| 2 | 35.9 ± 3.0 |
| 4 | 58.2 ± 4.9 |
| 6 | 74.4 ± 5.4 |
| 8 | 84.0 ± 6.2 |

The conventional tablet formulation of α-dihydroergocryptine 40 mg had the following composition: α-dihydroergocryptine, 40.0 mg; lactose, 128 mg; microcrystalline cellulose, 70 mg; croscarmellose, 6 mg; magnesium stearate, 4 mg; and polyvinylpyrrolidone, 2 mg. The dissolution test was carried out in the same conditions as for the sustained-release formulation of the present invention described in this example and resulted in 93.3±5.0% release of α-dihydroergocryptine after 0.5 hours.

Example 4

α-Dihydroergocryptine 40 mg Sustained-Release Tablets

Composition of Each Tablet

| | |
|---|---|
| α-Dihydroergocryptine | 40.0 mg |
| Lactose DCL11 ® | 105.0 mg[1] |
| Avicel PH101 ® | 76.0 mg[2] |
| Carbopol 934P ® | 25.0 mg[3] |
| Magnesium stearate | 4.0 mg |

Notes:
[1]Sprayed dried lactose, commercially available from Meggle GmbH of Wasserburg, Germany.
[2]Microcrystalline cellulose, commercially available from FMC Corporation, Pharmaceuticals Division, of Philadelphia, Pennsylvania.
[3]Carbomer, commercially available from BF Goodrich of Cleveland, Ohio.

Experimental Method

Tablets (250 mg) containing 40 mg (16%) each of α-dihydroergocryptine were prepared and tested according to the methods described hereafter. The formulation was prepared with 42% of lactose and 30.4% of microcrystalline cellulose, as direct compressible excipients, 10% of carbomer, as swellable controlled release polymer, and 1.6% of magnesium stearate, as lubricant.

The drug and all excipients except the lubricant were geometrically blended manually with a sieve, then mixed with a Turbula mixer for 10 minutes. After adding magnesium stearate, the mixture was blended for other 5 minutes. A rotary 8 station laboratory press with automatic powder feed and capsular tools (12×5 mm) was used for compression.

Tablet Testing

Standard pharmaceutical test methods and equipment were used to determine the following:
Hardness: average of 13.2 kp (Schleuniger 4M)
Friability: 0.2%
Dissolution test, according to USP XXIII, p. 1792, Apparatus 2, 1000 ml $H_2O$, 50 rotations/min:

| Time (hours) | % Release of α-Dihydroergocryptine (M ± SD) |
|---|---|
| 0.5 | 5.5 ± 0.9 |
| 1 | 11.2 ± 2.0 |
| 2 | 19.6 ± 6.1 |
| 4 | 30.0 ± 7.1 |
| 6 | 42.5 ± 3.3 |
| 8 | 56.2 ± 4.9 |

The conventional tablet formulation of α-dihydroergocryptine 40 mg had the same composition as in Example 3. The dissolution test was carried out in the same conditions as for the sustained release formulation of the present invention described in this example and resulted in 97.7±6.0% release of α-dihydroergocryptine after 0.5 hours.

Example 5

α-Dihydroergocryptine 10 mg Sustained-Release Tablets

Composition of Each Tablet

| | |
|---|---|
| α-Dihydroergocryptine | 10.0 mg |
| Cellactose ® | 184.3 mg[1] |
| Methocel K4M ® | 22.0 mg[2] |
| Methocel K15M ® | 9.7 mg[3] |
| Sodium CMC | 2.0 mg[4] |
| Talc | 20.0 mg |
| Magnesium stearate | 2.0 mg |

Notes:
[1]Composed of 75% lactose and 25% microcrystalline cellulose, commercially available from Meggle GmbH of Wasserburg, Germany.
[2]Hydroxypropylmethylcellulose USP type 2208; 4,000 mPa · s, commercially available from Colorcon of West Point, Pennsylvania.
[3]Hydroxypropylmethylcellulose USP type 2208; 15,000 mPa · s, commercially available from Colorcon of West Point, Pennsylvania.
[4]Medium viscosity grade.

Experimental Method

Tablets (250 mg) containing 10 mg (4%) each of α-dihydroergocryptine were prepared and tested according to the methods described hereafter. The formulation was prepared with 73.3% of Cellactose®, as direct compressible excipient, 8.8% of Methocel K4M®, 3.9% of Methocel K15M® and 0.8% ofسodium CMC as swellable controlled release polymers, 8% of Talc, as anti-sticking agent, and 0.8% of magnesium stearate, as lubricant.

The drug and all excipients except the lubricant were geometrically blended manually with a sieve, then mixed with a Turbula mixer for 10 minutes. After adding magnesium stearate, the mixture was blended for other 5 minutes. A rotary 8 station laboratory press with automatic powder feed and capsular tools (12×5 mm) was used for compression.

Tablet Testing

Standard pharmaceutical test methods and equipment were used to determine the following:
Hardness: average of 19.1 kp (Schleuniger 4M)
Friability: 0.26%
Dissolution test, according to USP XXIII, p. 1792, Apparatus 2, 500 ml 0.01 N HCl, 50 rotations/min:

| Time (hours) | % Release of α-Dihydroergocryptine (M ± SD) |
|---|---|
| 0.5 | 14.8 ± 1.0 |
| 1 | 23.6 ± 1.5 |
| 2 | 38.2 ± 1.6 |
| 4 | 60.9 ± 1.1 |
| 6 | 78.5 ± 3.9 |
| 8 | 89.3 ± 4.4 |
| 12 | 98.7 ± 3.8 |

The conventional tablet formulation of α-dihydroergocryptine 10 mg had the following composition: α-dihydroergocryptine, 10 mg; lactose, 158 mg; microcrystalline cellulose, 70 mg; croscarmellose, 6 mg; magnesium stearate, 4 mg; and polyvinylpyrrolidone, 2 mg. The dissolution test was carried out in the same conditions as for the sustained-release formulation of the present invention described in this example and resulted in 96.9±4.8% release of α-dihydroergocryptine after 0.5 hours.

Example 6

α-Dihydroergocryptine 10 mg Sustained-Release Tablets

Composition of Each Tablet

| | |
|---|---|
| α-Dihydroergocryptine | 10.0 mg |
| Cellactose ® | 216.0 mg[1] |
| Methocel K4M ® | 15.0 mg[2] |
| Methocel K15M ® | 5.0 mg[3] |
| Sodium CMC | 2.0 mg[4] |
| Magnesium stearate | 2.0 mg |

Notes:
[1]Composed of 75% lactose and 25% microcrystalline cellulose, commercially available from Meggle GmbH of Wasserburg, Germany.
[2]Hydroxypropylmethylcellulose USP type 2208; 4,000 mPa · s, commercially available from Colorcon of West Point, Pennsylvania.
[3]Hydroxypropylmethylcellulose USP type 2208; 15,000 mPa · s, commercially available from Colorcon of West Point, Pennsylvania.
[4]Medium viscosity grade.

Experimental Method

Tablets (250 mg) containing 10 mg (4%) each of α-dihydroergocryptine were prepared and tested according to the methods described hereafter. The formulation was prepared with 86.4% of Cellactose®, as direct compressible excipient, 6% of Methocel K4M®, 2% of Methocel K15M® and 0.8% of sodium CMC as swellable controlled release polymers, and 0.8% of magnesium stearate, as lubricant.

The drug and all excipients except the lubricant were geometrically blended manually with a sieve, then mixed with a Turbula mixer for 10 minutes. After adding magnesium stearate, the mixture was blended for another 5 minutes. A rotary 8 station laboratory press with automatic powder feed and capsular tools (12×5 mm) was used for compression.

Tablet Testing

Standard pharmaceutical test methods and equipment were used to determine the following:

Hardness: average of 16.1 kp (Schleuniger 4M)

Friability: 0.16%

Dissolution test, according to USP XXIII, p. 1792, Apparatus 2, 500 ml 0.01 N HCl, 50 rotations/min:

| Time (hours) | % Release of α-Dihydroergocryptine (M ± SD) |
|---|---|
| 0.5 | 24.7 ± 2.1 |
| 1 | 37.7 ± 2.8 |
| 2 | 58.3 ± 3.2 |
| 4 | 82.6 ± 3.9 |
| 6 | 92.9 ± 3.6 |
| 8 | 97.6 ± 1.8 |
| 12 | 100.00 ± 1.7 |

The conventional tablet formulation of α-dihydroergocryptine 10 mg had the same composition as in Example 5 and the dissolution test carried out in the same conditions as for the sustained release formulation of the present invention described in this example resulted in 93.7±3.1% release of α-dihydroergocryptine after 0.5 hours.

Example Comparing Bioavailability of Sustained-Release Formulations of the Present Invention with Bioavailability of Conventional Formulations

Example 7

The objective of the study was to evaluate in healthy volunteers the pharmacokinetic characteristics and the bioavailability of α-dihydroergocryptine in oral sustained-release tablets according to the present invention as described in Examples 5 and 6 in comparison to a conventional tablet according to the conventional tablet formulation described under Example 5. The study design was an open label, crossover, 3 period design. Twelve male volunteers were randomly assigned to one of three treatment sequences, separated by a one-week wash-out period. The drug was administered orally in the morning in fasted conditions (the fasted conditions were maintained for 4 hours after treatment) in a single dosage of 10 mg. Blood samples were obtained by an indwelling cannula at specific time points up to 72 hours after administration of the drug.

The plasma concentrations throughout the observation period are depicted in FIG. 2. The results of the pharmacokinetic analysis carried out on the plasma concentrations are reported in the Table (expressed as mean values).

| | Conventional Release Formulation (from Example 5) | Sustained-Release Formulation of Present Invention (from Example 5) | Sustained-Release Formulation of Present Invention (from Example 6) |
|---|---|---|---|
| $C_{max}$ (ng/L) | 147.0 | 65.1 | 58.2 |
| $T_{max}$ (h) | 1.3 | 4.6 | 8.0 |
| $T_{1/2}$ elim (h) | 14.8 | 27.9 | 42.8 |
| $AUC_{tot}$ (ng · h/L) | 865.1 | 1107.0 | 1894.5 |

These data clearly show that both the sustained-release formulations significantly reduce and delay the peak concentration, particularly for the sustained-release formulation described in Example 6. These figures express a slow absorption rate and a dramatic reduction of the burst which usually occurs after administration of a conventional formulation.

A three-fold increase of the elimination half-life is observed for the sustained-release formulation described in Example 6, an index of a prolonged absorption process as compared to the conventional tablet. The bioavailability of sustained release formulations of the present invention, as measured by AUC, is surprisingly higher than the bioavailability obtained with the conventional tablet.

The foregoing is illustrative of the present invention and is not to be construed as limiting thereof. The invention is defined by the following claims, with equivalents of the claims to be included therein.

Example 8

A composition according to the present invention has been prepared as follows:

| | | |
|---|---|---|
| α-Dihydroergocryptine Mesylate | 20.0 mg | 4% |
| Cellactose ® 80 | 368.6 mg | 73.72% |
| Methocel K4M ® | 44.0 mg | 8.8% |

| | -continued | |
|---|---|---|
| Methocel K15M ® | 19.4 mg | 3.88% |
| Carboxymethyl cellulose Sodium 7-HXF | 4.0 mg | 0.8% |
| Magnesium stearate Ph. Eur. | 4.0 mg | 0.8% |
| Talc Ph. Eur. | 40.0 mg | 8% |

Notes:
1. Composed of 75% lactose and 25% cellulose powder, commercially available from Meggle GmbH of Wasserburg, Germany.
2. Hydroxypropylmethylcellulose USP type 2208; 4,000 mPa · s, commercially available from Colorcon of West Point, Pennsylvania.
3. Hydroxypropylmethylcellulose USP type 2208; 15,000 mPa · s, commercially available from Colorcon of West Point, Pennsylvania.
4. Medium viscosity grade.

Experimental Method

The formulation was prepared mixing in a cube mixer (300 liter) for 15 minutes, 73.72% of Cellactose as direct compressible agent, 8.8% of Methocel K4M and 3.88% of Methocel K15M and 0.8% Carboxymethyl cellulose Sodium as swellable controlled release agents, 4% α-Dihydroergocryptine Mesylate as active ingredient and 8% Talc as filler. After adding 0.8% of Magnesium Stearate the blend was mixed for further 15 minutes. The blend is then pressed on a rotary tabletting machine (Ronchi 23N) equipped with punches Ø 12 mm.

Tablet Testing

Standard pharmaceutical test methods and equipment were used to determine the following:

Hardness: 11.0 Kp (Schleuniger 4M)

Friability: 0.06%

Mean weight: 500 mg

Thickness: 5 mm

Dissolution test, according to USP <711>, Apparatus 2, 500 ml 0.01 N HCl, 50 rotations/min

| Time (hours) | % Release of α-dihydroergocryptine |
|---|---|
| after 1 | 31.7% |
| after 4 | 55.9% |
| after 8 | 80.9% |

The conventional tablet formulation of α-Dihydroergocryptine 20 mg had the following composition: α-Dihydroergocryptine Mesylate, 20 mg; lactose, 148 mg; microcrystalline cellulose, 70 mg; croscarmellose, 6 mg; magnesium stearate, 4 mg; and polyvinylpyrrolidone, 2 mg. The dissolution test was carried out in the same conditions as for the sustained-release formulation of the present invention described in this example and resulted in 96.52% release of α-Dihydroergocryptine after 0.5 hours.

A comparative sustained release capsule (109/7) has been prepared with the following composition (i.e. not according to the present invention):

| α-Dihydroergocryptine Mesylate | 20 mg | 5% |
|---|---|---|
| Lactose FU | 176 mg | 44% |
| (1)Aerosil 200 | 2 mg | 0.5% |
| (2)Precirol AT05 (glycerol distearate) | 20 mg | 5% |

| | -continued | |
|---|---|---|
| (3)Methocel E4M Premium | 180 mg | 45% |
| Magnesium stearate | 2 mg | 0.5% |
| Total | 400 mg | |

Notes:
(1)Composed of Silicon Dioxyde, commercially available from Giusto Faravelli SpA, Italy
(2)Glycerol distearate, commercially available from Giusto Faravelli SpA, Italy
(3)Hydroxypropylmethylcellulose USP type 2208, 4.000 mPa · s, commercially available from Colorcon of West Point, Pennsylvania.

Experimental Method

A pre-mixing composed of 5% α-Dihydroergocryptine Mesylate as active ingredient, 44% Lactose and 0.5% of Aerosil as fillers, was prepared through a sieve. To this blend 45% of Methocel E4M Premium and 5% Precitol AT05 were added and mixed for 10 minutes. After adding 0.5% of Magnesium Stearate the blend was mixed for further 15 minutes. Then the blend was encapsulated using a manual encapsulation machine.

Dissolution Test

The dissolution test has been performed according to USP XXIV, p. 1792, Apparatus 2, 500 ml 0.01 N HCl, 50 rotations/min:

| Time (hours) | % Release of α-Dihydroergocryptine |
|---|---|
| 1 | 20.2% |
| 2 | 31.8% |
| 4 | 48.1% |
| 6 | 58.0% |
| 8 | 68.6% |
| 20 | 94.2% |

A further comparative sustained-release capsule (109/8) has been prepared with the following composition (i.e. not according to the present invention):

| α-Dihydroergocryptine | 20 mg | 5% |
|---|---|---|
| Lactose FU | 56 mg | 14% |
| (1)Aerosil 200 | 2 mg | 0.5% |
| (2)Precirol AT05 (glycerol distearate) | 200 mg | 50% |
| (3)Methocel E4M Premium | 120 mg | 30% |
| Magnesium stearate | 2 mg | 0.5% |
| Total | 400 mg | |

Notes:
(1)Composed of silicon Dioxyde, commercially available from Giusto Faravelli SpA, Italy
(2)Glycerol distearate, commercially available from Giusto Faravelli SpA, Italy
(3)Hydroxypropylmethylcellulose USP type 2208, 4.000 mPa · s, commercially available from Colorcon of West Point, Pennsylvania.

Experimental Method

A pre-mixed composed of 5% α-Dihydroergocryptine Mesylate as active ingredient, 14% Lactose and 0.5% of Aerosil as fillers, was prepared through a sieve. To this blend 30% of Methocel E4M Premium and 50% Precirol AT05 were added and mixed for 10 minutes. After adding 0.5% of Magnesium Stearate the blend was mixes for further 15 minutes. Then the blend was encapsulated using a manual machine.

Dissolution Test

The dissolution test has been performed according to USP XXIV, p. 1792, Apparatus 2, 500 ml 0.01 N HCl, 50 rotations/min:

| Time (hours) | % Release of α-Dihydroergocriptine |
|---|---|
| 1 | 14.6% |
| 2 | 25.5% |
| 4 | 39.3% |
| 6 | 48.6% |
| 8 | 59.1% |
| 20 | 88.4% |

Example 9

Comparative Clinical Test

The objective of this study was to evaluate in healthy volunteers the pharmacokinetik characteristic and the bioavailability of α-dihydroergocriptine in oral sustained-release tablets according to the present invention as described in Example 8 ("B") in comparison to: a conventional tablet according to the conventional tablet formulation described in Example 8 ("A"), the first comparative sustained-release capsule prepared according to the method described in Example 8 (109/7)("C"), and the second sustained-release capsule prepared according to the formulation described in Example 8 (109/8) ("D").

The study has been divided into two phases. In a first phase, the pharmacokinetics of "A" and "B" have been compared in an open label, crossover, 2 period design. Twelve male volunteers were randomly assigned to the two treatment sequences, separated by a one-week wash-out period. The drug was administered orally in the morning in fasted conditions in a single dosage of 20 mg. Blood samples were obtained by an indwelling cannula at specific time points up to 72 hours after administration of the drug.

The results of the pharmacokinetic analysis carried out on the plasma concentrations are reported in the Table (expressed as mean values).

|  | "A" Conventional Release Formulation (from Example 8) | "B" Substained-Release Formulation of Present Invention (from Example 8) |
|---|---|---|
| $C_{max}$ (ng/L) | 410.4 | 139.9 |
| $T_{max}$ (h) | 0.6 | 7.1 |
| $AUC_{0 \to t}$ (ng h/L) | 852.7 | 2086.8 |

In the second phase, the pharmacokinetics of "A"; "C" and "D" have been compared in an open label, crossover, 3 period design. Six male volunteers were randomly assigned to the three treatment sequences, separated by a one-week wash-out period. The drug was administered orally in the morning in fasted conditions in a single dosage of 20 mg. Blood samples were obtained by an indwelling cannula at specific time points up to 722 hours after administration of the drug.

The results of the pharmacokinetic analysis carried out on the plasma concentrations are reported in the Table (expressed as mean values).

|  | "A" Conventional Release Formulation (from Example 8) | "C" Substained-Release Formulation 109/7 (from Example 8) | "D" Substained-Release Formulation 109/8 (from Example 8) |
|---|---|---|---|
| $C_{max}$ (ng/L) | 742.8 | 159.1 | 47.9 |
| $T_{max}$ (h) | 0.8 | 5.7 | 9.7 |
| $AUC_{0 \to t}$ (ng h/L) | 2121.3 | 2212.8 | 1060.5 |

These data clearly show that all the sustained-release formulations, namely "B", "C" and "D" from Example 8, significantly reduce and delay the peak concentration. These figures express a slow absorption rate and a dramatic reduction of the burst which usually occurs after administration of a conventional formulation.

The bioavalability measured by AUC of the comparative sustained release formulation "C" and "D" from Example 8, is similar or lower to that of the conventional tablet "A" from Example 8. On the contrary, the bioavalability of sustained release formulations of the present invention, as measured by AUC, is surprisingly higher than the bioavalability obtained with the conventional tablet.

What is claimed is:

1. A method of improving bioavailability of α-dihydroergocryptine administered using sustained-release delivery systems comprising combining α-dihydroergocryptine, optionally in a salt form or mixture thereof, with a pharmaceutically acceptable hydrophilic swelling agent mixture and one or more pharmaceutically acceptable excipients, wherein the ratio of α-dihydroergocryptine to said hydrophilic swelling agent mixture is 1:2 to 1:4 by weight and wherein the hydrophilic swelling agent is a mixture of carboxymethylcellulose and two types of hydroxypropylmethylcellulose, wherein the first type of hydroxypropylmethylcellulose has a 19-24 weight percent methoxy content, a viscosity of 4,000 cps in a 2% water solution and a weight average molecular weight of 89,000 daltons and wherein the second type of hydroxypropylmethylcellulose has a 19-24 weight percent methoxy content, a viscosity of 15,000 cps in a 2% water solution and a weight average molecular weight of 124,000 daltons.

2. The method according to claim 1, wherein the ratio of α-dihydroergocryptine to said one or more pharmaceutically acceptable excipients is from 1:5 to about 1:80.

3. The method according to claim 1, wherein the ratio of α-dihydroergocryptine to said one or more pharmaceutically acceptable excipients is from about 1:10 to about 1:50.

4. The method according to claim 1, wherein the one or more pharmaceutically acceptable excipients is selected from the group consisting of fillers, cellulose preparations and lubricants.

5. The method according to claim 1, wherein the α-dihydroergocryptine is in an amount from about 5 to about 80 mg.

6. The method according to claim 1, wherein the α-dihydroergocryptine is used in the form of its mesylate salt.

7. The method according to claim 4, wherein said filler is selected from the group consisting of lactose, cellulose and talc.

8. The method according to claim 4, wherein said lubricant is magnesium stearate.

9. The method according to claim 4, wherein the one or more pharmaceutically acceptable excipients is selected from the group consisting of lactose, sucrose, mannitol, sorbitol, microcrystalline cellulose, maize starch, wheat starch, rice starch, potato starch, gelatin, tragacanth gum, polyvinylpyrrolidone (PVP) and magnesium stearate.

* * * * *